United States Patent [19]

Adjei et al.

[11] Patent Number: 4,851,211

[45] Date of Patent: Jul. 25, 1989

[54] LHRH ANALOG FORMULATIONS

[75] Inventors: Akwete L. Adjei, Wadsworth; Edwin S. Johnson, Antioch; James W. Kesterson, Libertyville, all of Ill.

[73] Assignee: Abbott Laboratories, Abbott Park, Ill.

[21] Appl. No.: 934,874

[22] Filed: Nov. 25, 1986

[51] Int. Cl.$^4$ ............................................. A01N 25/06
[52] U.S. Cl. ........................................ 424/40; 424/45; 424/47; 424/435; 514/15; 530/313
[58] Field of Search ..................... 424/45, 47, 40, 435; 514/15; 530/313

[56] References Cited

U.S. PATENT DOCUMENTS

| | | | |
|---|---|---|---|
| 4,248,864 | 2/1981 | Jones | 530/313 |
| 4,392,996 | 7/1983 | Sternberger | 530/313 |
| 4,476,116 | 10/1984 | Anik | 530/313 |
| 4,675,189 | 6/1987 | Kent et al. | 424/490 |
| 4,705,778 | 11/1987 | Almquist et al. | 514/15 |

FOREIGN PATENT DOCUMENTS

| | | |
|---|---|---|
| 0111841 | 6/1984 | European Pat. Off. . |
| 2054603 | 2/1981 | United Kingdom ............... 530/313 |

*Primary Examiner*—Ellis P. Robinson
*Assistant Examiner*—P. J. Ryan
*Attorney, Agent, or Firm*—Steven F. Weinstock; Martin L. Katz; Steven R. Crowley

[57] ABSTRACT

The invention relates to novel aerosol formulations comprising LHRH analogs, a lipophilic counterion, solvent and propellant and, optionally, surfactant, valve lubricant, an antioxidant and flavor and fragrance.

11 Claims, No Drawings

LHRH ANALOG FORMULATIONS

TECHNICAL FIELD

The invention relates to novel formulations comprising LHRH (luteinizing hormone releasing hormone) analogs and, more particularly, to LHRH analog aerosol formulations.

BACKGROUND ART

Polypeptides and LHRH analogs in particular are historically administered parenterally because they are poorly absorbed by biological membranes due to their large molecular size and polarity, enzymatic degradation and deactivation by proteases enroute to the circulatory system. To improve bioavailability, some have developed formulations for rectal and nasal administration. These two routes of administration yield bioavailability results of about 0-5% and are not reproducible. Thus, these routes are pharmaceutically unacceptable.

Further, to date no aerosol formulation has been developed for administration of LHRH analogs by inhalation. This is due in part because many peptide drugs such as LHRH agonist and antagonist compounds do not appreciably dissolve in hydrophobic liquid vehicles.

For example, leuprolide is a polar nonapeptide with three ionizable sites, namely the imidazolyl nitrogen of histidine with pKa approximately 6.0, the phenolic hydroxyl of tyrosine with pKa approximately 10.0, and the guanidine nitrogen of arginine with pKa approximately 13.0. Since the guanidine nitrogen is extremely basic, this nonapeptide as synthesized exists in the protonated form and is generally associated with at least one mole of acetic acid. Leuprolide, therefore, exists as an acetate salt, which is highly hydrophilic.

LHRH analogs are practically insoluble in fluorocarbons. In mixtures of ethyl alcohol and fluorocarbons, the solubility of leuprolide approaches 3 mg/ml which is not satisfactory due to dose requirements. This solubility estimate is not significantly affected by the presence of nonionic surfactants because, in part, of solubility and dielectric limitations of such surfactants. In mixtures of fluorocarbons, ethyl alcohol and water, experimental results showed equilibrium solubility of leuprolide to approach 5 mg/ml which is still unacceptable. At high concentrations of ethyl alcohol, a gel-like mass forms resulting in a colloidal dispersion that does not clear at room temperature for up to one month. At water concentrations of 10% or greater, a complete phase separation occurs making a homogeneous formulation impractical and renders aerosolization impractical.

DISCLOSURE OF THE INVENTION

It has now been discovered that the foregoing and other problems with the prior art can be overcome by including lipophilic counterions in solvent-based aerosol formulations. Bioavailability of leuprolide, a prototype peptide in this invention, ranges from 50% to 100% of the intravenously administered product as a control formulation. Time for plasma peak concentration to occur is about 30 minutes, and the plasma peak concentration itself approximately equals that of a comparable dose administered intravenously.

In particular, the aerosol formulations for administration of LHRH analogs comprises:
1. LHRH analogs (active ingredient)
2. lipophilic counterion (solubilizing agent)
3. surfactant (wetting agent)
4. solvent
5. propellant and optionally
6. valve lubricant
7. antioxidant
8. flavor/fragrance.

More particularly, the preferred formulation of the invention is as follows:

| Ingredient | Amount/ 1000 ml | Ranges |
| --- | --- | --- |
| Ethyl Alcohol, Dehydrated, USP, 100 Proof | 355.00 ml | 0.50-60.00% w/w |
| Sorbitan Monooleate, NF | 15.00 gm | 0.05-6.00% w/w |
| Water, Purified, USP (Distilled) | 40.00 ml | 0.10-15.00% w/w |
| 1-Decane Sulfonic Acid Sodium Salt | 2.00 gm | 0.01-2.00% w/w |
| Leuprolide Acetate | 5.30 gm | 0.01-2.00% w/w |
| Dichlorodifluoromethane | q.s | q.s |

BEST MADE FOR CARRYING OUT THE INVENTION

The aerosol composition for administration of LHRH analogs by inhalation comprises:

| Ingredient | Range |
| --- | --- |
| LHRH Analog | .001-15 mg/g |
| Lipophilic Counterion | .05-10 mg/g |
| Surfactant | 0-5% w/w |
| Solvent (Water and Ethyl Alcohol) | 10-50% w/w |
| Propellant | q.s |

As used herein, "% w/w" refers to weight of ingredient per weight of formulation multiplied by 100.

As used herein, the term "LHRH analog" refers to octapeptides, nonapeptides and decapeptides including but not limited to leuprolide, D-amino acid analogs of LHRH and leuprolide at the 6-position and/or 9-position.

As used herein, the term "leuprolide" or "leuprolide acetate" refers to a nonapeptide, 5-Oxo-L-prolyl-L-histidyl-L-tryptophanyl-L-seryl-L-tyrosyl-D-leucyl-L-leucyl-L-arginyl-L-prolylethylamide acetate with the structure:

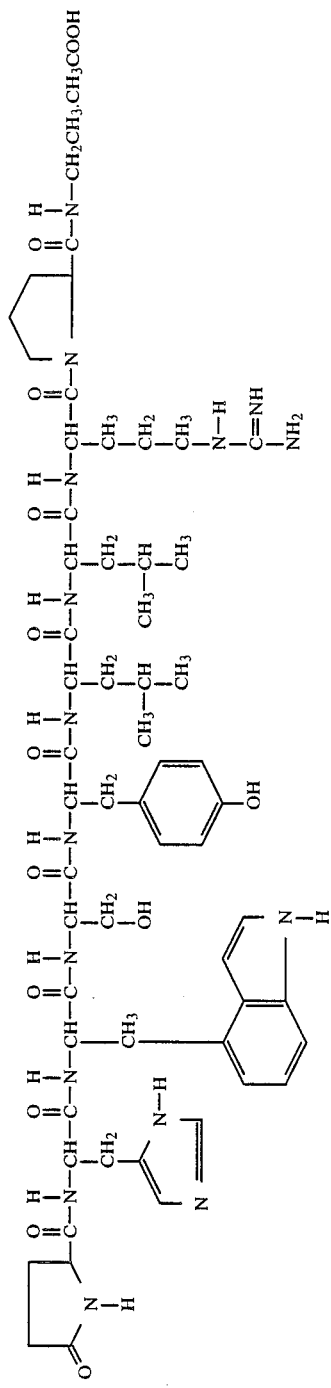

As used herein, the term "surfactant" refers to nonionic surfactants including but not limited to mono and diglycerides, sorbitan fatty acid esters, polyoxyethylene sorbitan fatty acid esters, polyoxyethylene sorbitol esters, polyoxyethylene acids, polyoxyethylene alcohols and polyoxyethylene adducts.

As used herein, the term "lipophilic counterion or "counterion" refers to organic acids or their salts with pka sufficiently low to render them ionizable at the product pH and includes but is not limited to alkyl ($C_5$–$C_{12}$) sulfonic acids and salts thereof, palmitates, dioctylsulfosuccinate and its congeners, stearates and salicylates.

As used herein, the term "propellant" refers to chlorofluorocarbons or hydrocarbons including but not limited to trichlorofluoromethane, dichlorodifluoromethane, chlorodifluoromethane and dichlorotetrafluoromethane.

The presence of various lipophilic counterions significantly improves the equilibrium solubility of the LHRH analog in many cosolvent systems studied. Increasing concentrations of the counterion generally increases the solubility of LHRH analog in the propellant solvent systems. However, this is limited by the intrinsic solubility of the counterion itself. Thus, high concentrations of the counterion can be detrimental to the clarity and stability of the solution.

Optimal concentrations of the counterion of choice, decane sodium sulfonate, is 2 mg/ml. At this concentration, the equilibrium solubility of the LHRH analog in appropriate cosolvent mixtures of ethyl alcohol and dichlorodifluoromethane is about 20 mg/ml. However, a formulation containing 10 mg/ml of leuprolide appears to possess all desired physical characteristics of a satisfactory/stable aerosol.

In general, other lipophilic counterions also significantly improve the solubility of LHRH analogs in a propellant-water-ethanol cosolvent system. The most preferred counterions are: alkyl sulfonates followed by palmitates, dioctylsulfosuccinates, stearates and salicylates. These findings correlate with counterion pKa and appear to be consistent with drug distribution phenomena.

A product containing approximately 25.0% w/w ethyl alcohol, 1.3% w/w sorbitan monooleate, 0.2% w/w decane sulfonic acid (sodium salt), 3.5% w/w water, 1.0% leuprolide acetate, and 69% w/w dichlorodifluoromethane is the preferred formulation for a leuprolide solution aerosol product. This formulation has good spray characteristics and has satisfactory physical and chemical stability.

The compositions of the invention can be prepared by cold filling or pressure filling.

Cold filling comprises the steps as follows:

(a) Mix alcohol and water in stainless steel or glass vessel.
(b) Add LHRH analog and counterion. Mix well until completely dissolved.
(c) Add surfactant. Mix well to dissolve.
(d) Filter through appropriate filter to clarify solution.
(e) Transfer to pressure vessel. Chill solution to approximately 0° C. or lower.
(f) Add appropriate propellant as liquefied gas. Mix well until a uniform solution forms.
(g) Fill into appropriate containers.

Pressure filling comprises the steps as follows:

(a) Mix alcohol and water in stainless steel or glass vessel.
(b) Add LHRH analog and counterion. Mix well until completely dissolved.
(c) Add surfactant. Mix well to form complete solution.
(d) Filter if necessary using appropriate filter.
(e) Fill appropriate volume into aerosol container and crimp valves onto container.
(f) Fill appropriate volume of liquified propellant into container through the valve. Check for leaks in warm water bath.

The foregoing may be better understood from the following examples which are presented for purposes of illustration and are not intended to limit the scope of the invention.

EXAMPLE 1–15

Following the cold filling procedure outlined above and utilizing the ingredients referred to at numbers 1–15 on Table 1, gave the compositions referred to in Table 1.

SOLUBILITY TESTING

Weighed quantities of leuprolide and the counterion were placed into 20 ml glass vials provided with rubber stoppers and appropriate overseals. The measured quantities of the liquified propellants were added to the vials. In systems where water and/or alcohol were used, the appropriate volumes of these liquids were measured and added. The prepared vials were sealed and shaken to determine equilibrium concentration of the LHRH analog in these respective solvent systems.

Results of the limit solubility measurements obtained with leuprolide in the respective solvents are reported in Table 1. These solubility results are pharmaceutically acceptable. The results are reported as estimates since propellant pressures often presented sampling problems which in turn prevented actual determination of the limit solubility for the LHRH analog and since these solutions were not saturated due to their high affinity for leuprolide acetate.

TABLE 1

Effect of Lipophilic Counterions on Leuprolide Solubility at 25° C.

| | Liquid Vehicle Composition | | | | | | |
|---|---|---|---|---|---|---|---|
| Example # | Water % v/v | Ethyl Alcohol, % v/v | Dichloro fluorocarbon % v/v | Counterion, % w/v DSASS | PA | DOSS | Solubility of leuprolide (mg/ml) |
| 1 | 4.0 | 50.0 | 46.0 | 0.2 | | | >10 |
| 2 | 4.0 | 50.0 | 46.0 | | 0.2 | | >5 |
| 3 | 4.0 | 50.0 | 46.0 | | | 0.2 | >8 |
| 4 | 4.0 | 45.0 | 51.0 | 0.2 | | | >10 |
| 5 | 4.0 | 45.0 | 51.0 | | 0.2 | | >5 |
| 6 | 4.0 | 45.0 | 51.0 | | | 0.2 | >8 |
| 7 | 4.0 | 40.0 | 56.0 | 0.2 | | | >10 |
| 8 | 4.0 | 40.0 | 56.0 | | 0.2 | | >5 |

TABLE 1-continued Effect of Lipophilic Counterions on Leuprolide Solubility at 25° C.

| Example # | Liquid Vehicle Composition | | | | | | Solubility of leuprolide (mg/ml) |
|---|---|---|---|---|---|---|---|
| | Water % v/v | Ethyl Alcohol, % v/v | Dichloro fluorocarbon % v/v | Counterion, % w/v | | | |
| | | | | DSASS | PA | DOSS | |
| 9 | 4.0 | 40.0 | 56.0 | | | 0.2 | >6 |
| 10 | 4.0 | 35.0 | 61.0 | 0.2 | | | >10 |
| 11 | 4.0 | 35.0 | 61.0 | | 0.2 | | >5 |
| 12 | 4.0 | 35.0 | 61.0 | | | 0.2 | >6 |
| 13 | 4.0 | 30.0 | 66.0 | 0.2 | | | >8 |
| 14 | 4.0 | 30.0 | 66.0 | | 0.2 | | >5 |
| 15 | 4.0 | 30.0 | 66.0 | | | 0.2 | >6 |

DSASS = Decane Sulfonic Acid Sodium Salt
PA = Palmitic Acid
DOSS = Dioctyl Sulfosuccinate

BIOABSORPTION TESTING

Healthy male beagle dogs (9–18 months old) were provided with free access to food during entire study. There were three dogs of each sex in each treatment group. Body weight, food consumption and other pertinent clinical signs were monitored at a regular basis during the study. By surgical procedure, tracheal stoma was performed to each dog. On the day of the study, the dogs were administered solution aerosol of leuprolide acetate of Example 10 except with 0.5, 1.0, and 2.0 mg of leuprolide. Drug administration was carried out through 2 weeks. Leuprolide plasma concentrations was determined during day 1 of the study in order to evaluate bioabsorption of leuprolide from the aerosol. Blood samples of approximately 2–3 ml were obtained from the jugular vein and allowed to clot. After centrifugation, the serum fraction was removed and assayed for leuprolide using a radioimmunoassay technique. Relative absorption of leuprolide via the inhalation route of administration was estimated using mean historical data from representative intravenously administered formulations. Table II shows the results of the above testing and indicates virtually complete absorption of leuprolide.

TABLE II

Plasma Concentrations of Leuprolide (Ng/ml) Following Inhalation Delivery of Leuprolide Aerosolized Formulation

| Dog No. | Plasma Concentrated (Ng/Ml) Over Time (Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 25.7 | 36.2 | 26.9 | 7.7 | 3.6 | 0.9 | 54.2 |
| 2 | 0.0 | 23.7 | 24.7 | 16.1 | 5.8 | 2.8 | 0.8 | 38.1 |
| 3 | 0.0 | 38.3 | 44.3 | 35.3 | 13.1 | 6.7 | 1.8 | 77.6 |
| 4 | 0.0 | 23.0 | 42.1 | 34.6 | 11.6 | 4.3 | 1.2 | 66.7 |
| 5 | 0.0 | 40.1 | 51.1 | 39.5 | 14.7 | 7.0 | 2.0 | 86.0 |
| 6 | 0.0 | 84.8 | 72.5 | 48.2 | 17.7 | 8.2 | 2.0 | 116.5 |
| Mean | 0.0 | 39.3 | 45.2 | 33.4 | 11.8 | 5.4 | 1.5 | 73.2 |
| S.D. | 0.0 | 23.5 | 16.1 | 11.0 | 4.4 | 2.2 | 0.6 | 27.2 |

Dose = 0.5 mg
Relative bioavailability = 87.4%

| Dog No. | Plasma Concentration (Ng/Ml) Over Time (Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 89.6 | 118.9 | 79.5 | 28.3 | 13.5 | 4.0 | 179.2 |
| 2 | 0.0 | 85.0 | 50.5 | 34.2 | 11.1 | 5.2 | 1.2 | 85.9 |
| 3 | 0.0 | 91.7 | 102.4 | 75.0 | 30.5 | 13.2 | 3.8 | 171.7 |
| 4 | 0.0 | 88.3 | 118.4 | 96.3 | 33.3 | 19.1 | 5.9 | 206.6 |
| 5 | 0.0 | 78.7 | 91.0 | 56.3 | 18.1 | 7.9 | 1.8 | 127.8 |
| Mean | 0.0 | 86.7 | 96.2 | 68.3 | 24.3 | 11.8 | 3.3 | 154.2 |
| S.D. | 0.0 | 5.1 | 28.1 | 23.8 | 9.3 | 5.4 | 1.9 | 47.5 |

Dose = 1.0 mg
Relative bioavailability = 92.1%

| Dog No. | Plasma Concentration (Ng/Ml) Over Time (Hours) | | | | | | | AUC (Ng/Hr/Ml) |
|---|---|---|---|---|---|---|---|---|
| | 0 | 0.25 | 0.50 | 1.00 | 2.00 | 3.00 | 5.00 | |
| 1 | 0.0 | 136.4 | 165.2 | 181.0 | 75.7 | 44.4 | 12.8 | 386.9 |
| 2 | 0.0 | 148.3 | 225.4 | 131.7 | 48.9 | 20.7 | 5.7 | 306.0 |
| 3 | 0.0 | 178.1 | 167.9 | 148.2 | 69.1 | 31.9 | 7.5 | 343.1 |
| 4 | 0.0 | 121.9 | 138.7 | 72.7 | 22.6 | 10.3 | 2.0 | 177.1 |
| 5 | 0.0 | 204.6 | 258.4 | 194.7 | 125.7 | 71.0 | 22.8 | 549.1 |
| 6 | 0.0 | 91.8 | 104.0 | 88.9 | 37.8 | 16.8 | 3.9 | 195.5 |
| 7 | 0.0 | 125.8 | 118.7 | 95.4 | 43.1 | 17.4 | 4.2 | 220.9 |
| Mean | 0.0 | 143.8 | 168.3 | 130.4 | 60.4 | 30.4 | 8.4 | 311.2 |
| S.D. | 0.0 | 37.5 | 56.1 | 47.1 | 34.0 | 21.2 | 7.2 | 131.0 |

Dose = 2.0 mg
Relative bioavailability - 93.1%

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. An aerosol formulation comprising 0.001–15 mg/g of LHRH analog, 0.05–10 mg/g of a lipophilic counterion selected from alkyl ($C_5$–$C_{12}$) sulfonic acid or salts thereof, 0.1–15% w/w water, 0.5–60% w/w ethyl alcohol and q.s. propellant.

2. The formulation of claim 1 wherein the LHRH analog is leuprolide acetate.

3. The formulation of claim 1 wherein the alkyl sulfonic acid is selected from decane sulfonic acid or a salt thereof.

4. An aerosol formulation comprising 0.01–2% w/w of al LHRH analog, 0.01–2% w/w of a lipophilic counterion selected from alkyl ($C_5$–$C_{12}$) sulfonic acid or salts thereof, 0.5–50% w/w ethyl alcohol, 0.1–15% w/w water, 0.05–6% w/w of a surfactant and q.s. propellant.

5. The formulation of claim 4 wherein the LHRH analog is leuprolide acetate.

6. The formulation of claim 1 wherein the alkyl sulfonic acid is selected from decane sulfonic acid or a salt thereof.

7. The formulation of claim 4 wherein the surfactant is sorbitan monoleate.

8. The formulation of claim 4 wherein the propellant is a chlorofluorocarbon.

9. The formulation of claim 8 wherein the chlorofluorocarbon is dichlorodifluoromethane.

10. An aerosol formulation comprising 0.01–2% w/w leuprolide acetate, 0.01–2% w/w 1-decane sulfonic acid sodium salt, 0.5–50% w/w ethyl alcohol, 0.1–15% w/w water, 0.05–6% w/w sorbitan monooleate, and q.s. dichlorodifluoromethane.

11. The aerosol formulation of claim 10 comprising 25% w/w ethyl alcohol, 1.3% w/w sorbitan monooleate, 0.2% w/w 1-decane sulfonic acid sodium salt, 3.5% w/w water, 1% w/w leuprolide acetate and 69% w/w dichlorodifluoromethane.

* * * * *

UNITED STATES PATENT AND TRADEMARK OFFICE
CERTIFICATE OF CORRECTION

PATENT NO. : 4,851,211
DATED : July 25, 1989
INVENTOR(S) : A. Adjei, et al.

It is certified that error appears in the above-identified patent and that said Letters Patent is hereby corrected as shown below:

Column 9, line 19, change "al LHRH" to --an LHRH--.

Column 10, line 3, change "claim 1" to --claim 4--.

Signed and Sealed this

Nineteenth Day of February, 1991

Attest:

HARRY F. MANBECK, JR.

*Attesting Officer*　　　*Commissioner of Patents and Trademarks*